United States Patent [19]

Latta

[11] Patent Number: 5,198,773
[45] Date of Patent: Mar. 30, 1993

[54] NON-INTRUSIVE GAS-LEVEL MEASUREMENT APPARATUS

[76] Inventor: Bryan M. Latta, P.O. Box 328, Wolfville, Nova Scotia, Canada, B0P 1X0

[21] Appl. No.: 634,058

[22] Filed: Dec. 26, 1990

[30] Foreign Application Priority Data

Dec. 21, 1990 [CA] Canada .................. 2032912

[51] Int. Cl.$^5$ .................. G01N 27/70
[52] U.S. Cl. .................. 324/464; 324/71.1; 324/72; 324/551; 340/632
[58] Field of Search .................. 324/464, 459, 71.1, 324/72, 551; 73/19.01; 340/632

[56] References Cited

U.S. PATENT DOCUMENTS

| | | | |
|---|---|---|---|
| 1,421,720 | 7/1922 | Roberts | 324/464 |
| 3,247,452 | 4/1966 | Kordesch | 324/71.1 X |
| 3,370,227 | 2/1968 | Bader et al. | 324/54 |
| 3,510,763 | 5/1970 | Clinton | 324/54 |
| 3,753,087 | 8/1973 | Tan | 324/52 |
| 3,775,676 | 11/1973 | Harrold et al. | 324/52 |
| 3,979,668 | 9/1976 | Samulowitz | 324/71.1 |
| 4,117,397 | 9/1978 | Fukao et al. | 324/54 |
| 4,366,437 | 12/1982 | Lombard | 324/464 |
| 4,373,375 | 2/1983 | Terhune et al. | 73/19.01 |
| 4,435,681 | 3/1984 | Masuda et al. | 324/459 |
| 4,478,704 | 10/1984 | Miyoshi et al. | 340/532 X |
| 4,629,992 | 12/1986 | Nudelmont | 324/464 |
| 4,894,251 | 1/1990 | Sieverin | 324/71.1 X |

FOREIGN PATENT DOCUMENTS

| | | | |
|---|---|---|---|
| 1155496 | 10/1983 | Canada | 324/59 |
| 1249338 | 1/1989 | Canada | 324/59 |

*Primary Examiner*—Kenneth A. Wieder
*Assistant Examiner*—Glenn W. Brown
*Attorney, Agent, or Firm*—Davis, Bujold & Streck

[57] ABSTRACT

A method of determining the percentage gas content of an insulating glass window unit or the like comprises the steps of applying a voltage to opposed panes of the unit, progressively increasing the voltage, monitoring the voltage and recording the magnitude of the voltage at which a continuous discharge occurs, or is about to occur, between the electrodes and converting the magnitude to a number indicative of the percentage gas content of the gas between the panes.

15 Claims, 2 Drawing Sheets

NON-INTRUSIVE GAS-LEVEL MEASUREMENT APPARATUS

The present invention relates to a method and an apparatus for determining the percent content of argon in insulating glass window units.

BACKGROUND OF THE INVENTION

To improve performance, some window manufacturers in North America fill their insulating glass windows with special gases. Typically, sulphur hexafluoride (SF6) is used where sound insulation is important and argon is used when thermal insulation is important. The benefits of thermal insulation are gaining universal acceptance by window manufacturers and consumers alike, since thermal performance enhancements of 10 to 25 percent can be achieved with an argon fill. On a national scale, this improvement is significant.

The present invention is concerned with the problem of monitoring the gas content of insulating glass units. Gas content measurements are desirable for several reasons: quality control at production, quality assurance at the construction site before and after installation, long term field tests, accelerated weathering studies, and so forth. Heretofore, the gas content of a window unit has been determined by puncturing the gas seal of the window unit to remove a sample of gas for analysis. The repair of the puncture is not necessarily as secure or reliable as the overall construction of the window unit and, accordingly, a better product can be obtained if a non-intrusive test was available for both quality control and long-term field-performance tests.

A known non-intrusive measurement technique involves focusing monochromatic light onto the gas in the window unit and observing the scattered light signal. Using the known Raman scattering phenomenon, the wavelength for resonant scattering off of either the oxygen or nitrogen molecules, a well defined signature of the presence of either gas, can be used to determine the quantity of air in the unit. With this technique, a precision of about 0.2 percent can be achieved after five scans. This technique does not measure argon directly. It must be calculated from the measured air content. Further drawbacks of this technique are that it requires vibration isolation, an optical table with expensive state of the art technology, a high level of technical expertise and it can only be used in laboratory applications at present. Accordingly, it is not a viable solution.

Another method of determining the gas content of a window unit is to measure its thermal conductance. This method provides a qualitative indication of whether the window unit is above 75 percent filled with argon and provides a quantitative indication if its fill level is below 75 percent. However, the method is slow and, as indicated, does not provide precise numbers above 75 percent argon content. Manufacturers achieve a 95-100 percent argon fill so that a typical leakage of less than 0.5 percent argon loss per year guarantees at least a 20 year life span for the unit before the argon content drops below 75 percent and thermal performance begins to deteriorate significantly. Hence, this method does not provide any sensitivity to gas content in the region of most interest. In addition, the variability of the energy efficient coatings on the glass will affect the thermal conductance and this effect might not be easily determined.

It is also possible to use acoustic techniques for measuring gas content. One acoustical method involves considering the unit as a resonant cavity and establishing a standing acoustic wave within the unit. The frequency and/or wavelength of the wave would be indicative of the gas content. However, it has been found that there are too many vibration modes, other than the fundamental cavity mode, for this method to yield useful results. Another acoustic technique involves measuring the "time-of-flight" of a sound pulse passed through the unit. While it has been found that a relatively high precision of about 2 percent can be achieved for heavy gases such as SF6, precision is only about 20 percent for light gases such as argon. Clearly, known acoustical techniques are not satisfactory for light gases like argon which is the most used gas.

There is a need for an inexpensive, fast and reliable method for non-intrusively determining the gas content of an insulating glass window unit, i.e. without destroying the integrity of the seal.

SUMMARY OF THE INVENTION

The present invention seeks to provide an inexpensive, portable method and apparatus for non-intrusively measuring the gas content of insulating glass window units.

One aspect of the present invention is broadly defined as a method of determining the percentage gas content of an insulating glass window unit or the like, comprising the steps of applying a voltage to opposed panes of the unit; progressively increasing the voltage; monitoring the voltage and recording the magnitude of the voltage at which the electrical breakdown in the gas occurs or is about to occur; and converting the magnitude to a number indicative of the percentage gas content of the gas between the panes.

Another aspect of the present invention is broadly defined as an apparatus for determining the percentage gas content of an insulating glass window unit or the like, comprising a step-up transformer having a primary coil having a pair of input terminals adapted to be connected to a controlled source of electrical energy and a secondary coil having a pair of output terminals for producing a high voltage thereacross, a pair of electrodes connected to the output terminals of the secondary coil for connection to opposed panes of the window unit, means for monitoring the voltage applied to the input terminals, means for monitoring the voltage applied to the electrodes either directly or by conversion of the voltage applied to the input terminals, means for detecting the breakdown voltage at which an electrical discharge occurs or is about to occur across the electrodes and means for converting the breakdown voltage to a value indicative of the percentage content of the gas contained within the unit.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
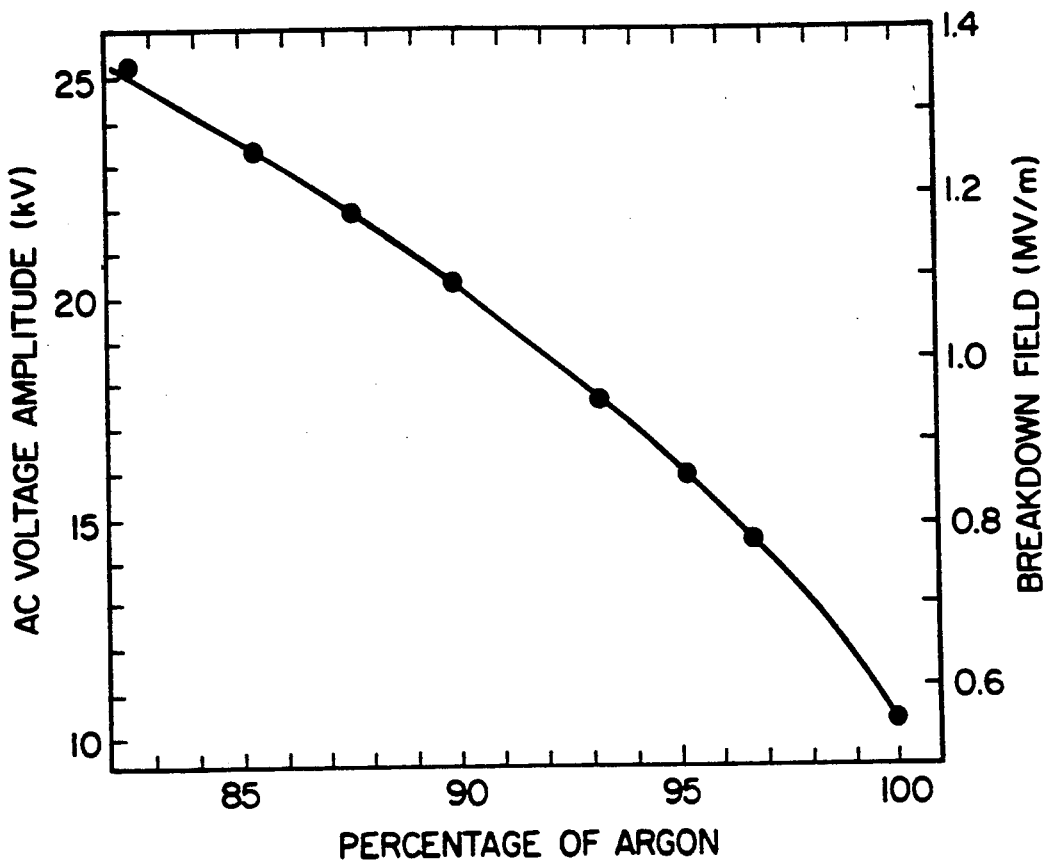
FIG. 1 is a graph showing the AC breakdown voltage on the electrodes in kV as a function of the percentage argon content of an insulating glass window unit over the range of 82 to 100 percent argon and the breakdown field which is characteristic of the argon-air gas mixture.

It has been found that the electrical breakdown voltage, the voltage at which an electrical discharge or spark occurs, in an argon containing chamber changes rapidly with the concentration of argon in the chamber. Thus, the argon content or concentration can be measured to a precision of about 0.1 percent in the region of interest simply by determining the breakdown voltage and converting the voltage to an argon content value. FIG. 1 graphically illustrates the relationship between the AC breakdown voltage on the electrodes in kV and the percentage argon content, over the range of 82 to 100 percent argon, for a particular insulating glass window unit. The graph also shows the relationship between the breakdown field in the gas and the argon concentration which can be applied to other window units. It will be noted that the breakdown voltage decreases rapidly with increasing argon content and that the largest changes occur at the high gas concentration end of the graph. The slope of the graph is such that for a gas fill over 80 percent argon, a 2 percent accuracy in measuring the voltage results in at least a 1 percent accuracy in determining the proportion of argon in the gas mixture. The slope is greatest near 100 percent argon content. This is highly desirable characteristic because it means that the greatest sensitivity and precision is in the region of interest.

Figure 2:
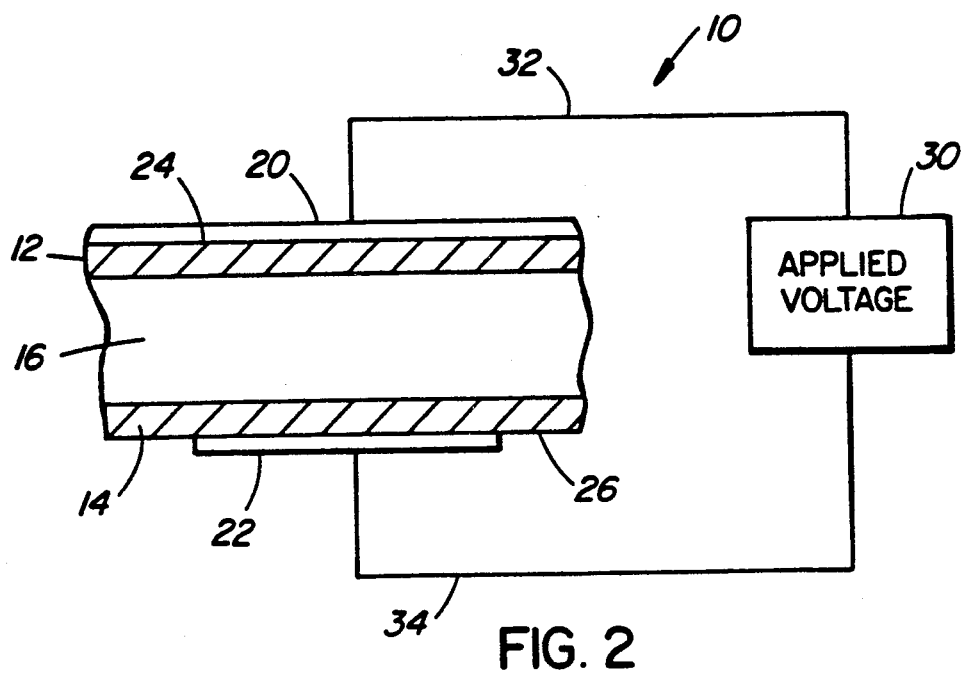
FIG. 2 is a broken cross-sectional view of a single double glazed insulating glass window unit showing a pair of electrodes secured to the outer surfaces of the two panes of glass and connected by suitable leads to a source of voltage.

FIG. 2 is a broken cross-sectional view of an insulating glass window unit 10 comprising two spaced apart panes of glass 12 and 14 which have been sealed, in the usual manner, along their edges (not shown) to form an interior chamber 16 filled with argon. In accordance with the present invention, two plate electrodes 20 and 22 are secured in firm contact with the outer surfaces 24 and 26 of panes 12 and 14, respectively, and connected to a source of voltage 30 by means of leads 32 and 34. According to the method of the present invention, an initially low voltage is applied to the electrodes and progressively increased until a continuous discharge occurs in the gas between electrodes. The voltage at or just prior to which the continuous discharge occurs, the breakdown voltage, is converted to an argon concentration value by referring to a relationship such as that illustrated in FIG. 1.

Figure 3:
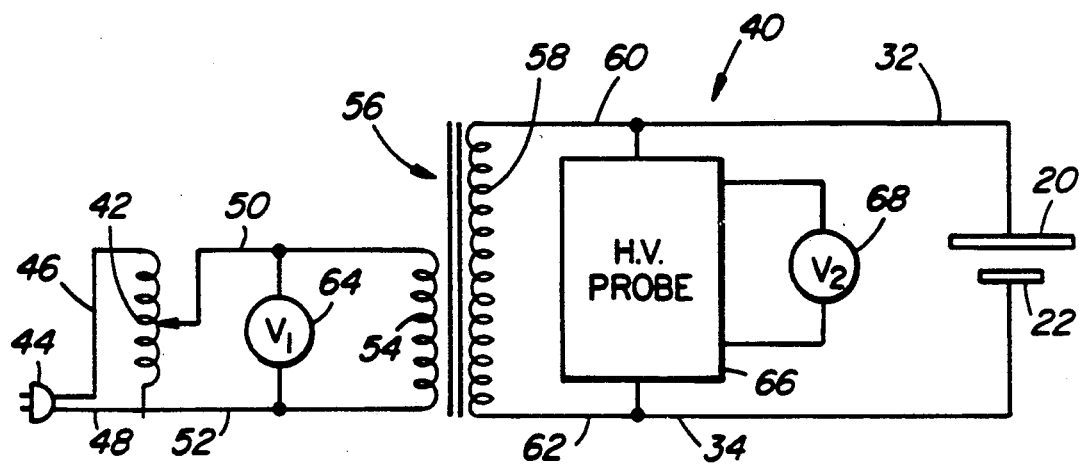
FIG. 3 is an electrical schematic of one embodiment of the present invention.

FIG. 3 is an electrical schematic of a one embodiment, generally designated by reference numeral 40, of the present invention. The circuit includes means capable of producing and controlling a voltage over the range of interest in the form of a variac 42 which is adapted to be connected to a standard 120 volt, 60 hz AC source by way of an electrical plug 44 and conductors 46 and 48. As indicated in FIG. 1, voltages on the order of about 30 kV are required to produce a continuous discharge in a 1.5 cm window gap. For window gaps that are typically 1 to 2.5 cm, voltages up to about 50 kV will be required to initiate electric breakdown in the gas. In order to generate voltages of this magnitude, the output terminals 50 and 52 of the variac are connected to the opposite terminals of the primary winding 54 of a step up transformer 56 comprised of the primary winding and a secondary winding 58. The output terminals 60 and 62 of the secondary winding are connected to aforementioned leads 32 and 34 which are connected to electrode 20 and 22, respectively. A volt meter 64 is connected across the output terminals of the variac so that the voltage delivered to the transformer can be monitored, while a high voltage probe 66 and a second volt meter 68 might be connected across the output terminals of the transformer secondary winding to calibrate the step up transformer so that a later measurement of the voltage on the primary side of the transformer can be related to the voltage on the secondary side which is applied to the plate electrodes. Thus, either voltage measurement can be used to determine the percent argon content.

The measured breakdown potential applied to the window unit is first converted to an electric breakdown field for the gas using known theory using the dielectric constant and dimension of each layer of glass and gas chamber. A gas calibration curve similar to FIG. 1 is used to relate this breakdown field to the gas mixture.

In operation, the applied voltage is increased at a uniform rate until a continuous or repetitive discharge occurs. Isolated discharges which occur occasionally may be ignored. The output voltage will be proportional to the input voltage until the breakdown voltage is reached where the output voltage shifts upon initiation of the discharge. At the same time the current to the electrodes on the secondary side of the transformer rapidly increases. Since the region between the electrodes is filled with a shower of discharges at breakdown, the onset of breakdown can be clearly identified by either visual inspection or by the associated sound. The voltages used for plotting the graph in FIG. 1 are voltages which were recorded just prior to breakdown.

The electrodes are preferably in the form of relatively large diameter conducting discs. Point electrodes would provide too small a volume within which the electric field reaches the breakdown value and, accordingly, the results obtained from using point electrodes would not be as reliable. On the other hand, the parallel-plate geometry provides a large constant-field region. Potential misalignment in the positioning of the electrodes is eliminated by having one electrode sufficiently large that it approximates an electrically infinite plane. As a safety precaution the electrode attachment should include a disabling switch (not shown) such that a voltage can only be applied while firm contact is made with the glass.

In instances where the glass has an infrared heat-reflecting conductive coating, which is known in the trade as a low-e or low emissivity or heat mirror or other coating, the procedure of allowing a continuous discharge might cause damage to the coating. Therefore, a means of limiting or avoiding damage to the coatings, such as prompt removal of the applied voltage at the onset of breakdown, current limiting circuitry or other means, should form part of the embodiment.

While the description thusfar has been with reference to a single double glazed unit, it is to be understood that the results can be applied to other multiple glazed units.

Figure 4:
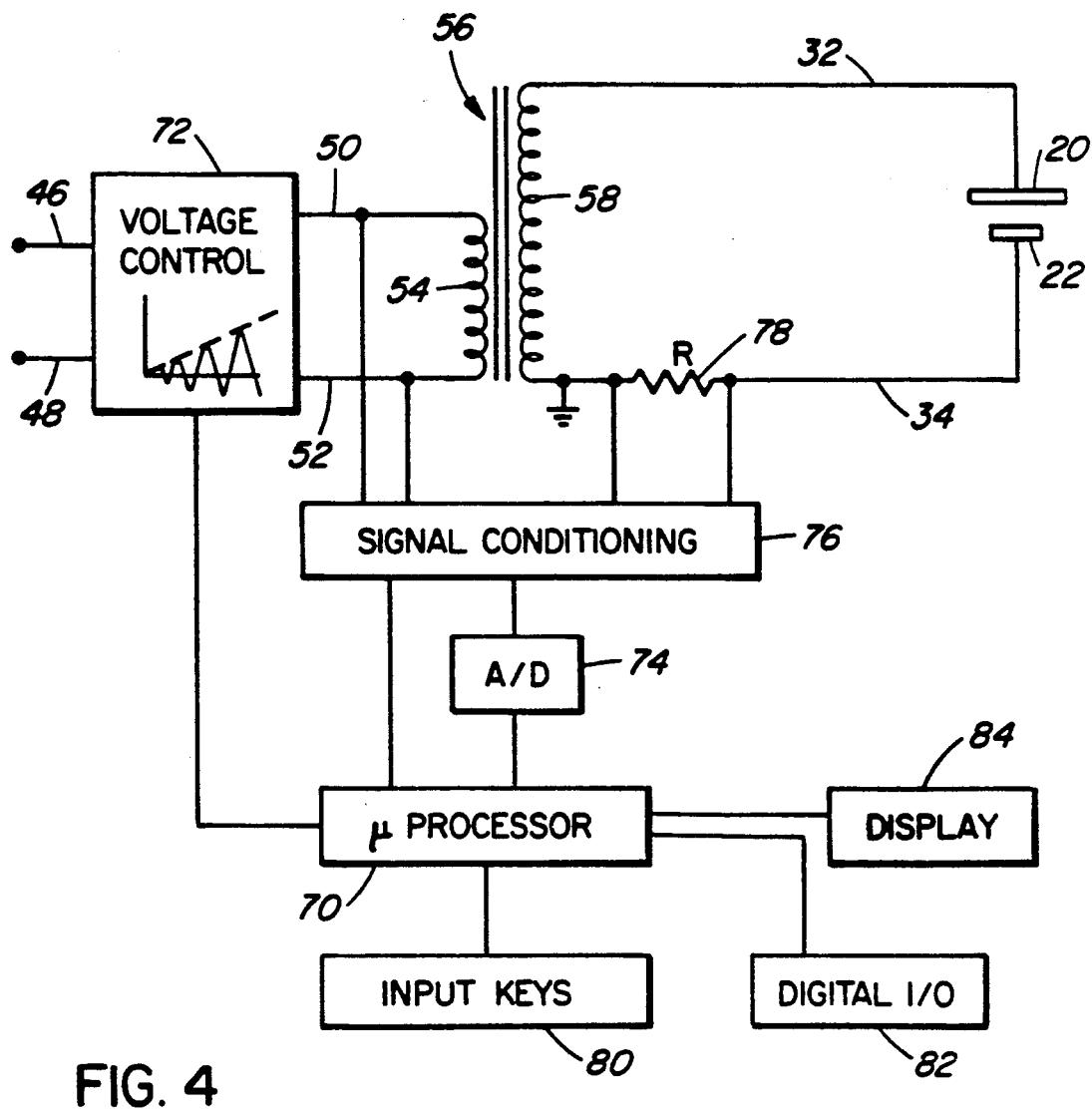
FIG. 4 is a block diagram representation of a preferred embodiment of the invention in which a microprocessor controls the input voltage and monitors the current to the electrodes to detect the onset or occurrence of breakdown.

FIG. 4 illustrates an alternative embodiment of the invention. In this embodiment there is provided a microprocessor circuit 70, a voltage control circuit 72 responsive to the control signals provided by the microprocessor circuit for producing an input voltage, an analog-to-digital convertor circuit 74 connected through signal conditioning circuits 76 either to the transformer primary winding terminals, or to a resistor 78, for digitizing the input voltage, or electrode current respectively, and delivering a digital representation thereof to the microprocessor circuit. It might be convenient to use more than one A/D converter. In operation, after the electrodes have been connected to the window unit in the manner explained earlier and the unit has been activated by a start key, the microprocessor delivers control signals to the voltage control circuit which causes the latter to progressively increase, at a predetermined rate, the amplitude of the AC voltage at its output terminals.

The means 72 of providing a controlled voltage to the primary windings terminals can include a motor-driven variac responsive to the microprocessor, or a manually adjusted variac, or other means of increasing the amplitude of the AC voltage output. Voltage control circuit 72 can be made to provide controlled termination of the voltage by means of a solid-state relay that switches on zero voltage cross over responsive to a signal from the microprocessor or any other control circuit.

Connections to the resistor, whose resistance is small compared to the resistance of the glass window, provide a means of monitoring the current to the electrodes via circuitry known to the art. The microprocessor or other circuitry keys on a change in the rate of change of the current relative to the rate of change of the input voltage in order to sense the onset of breakdown. It might be convenient to rectify both signals.

Connections to the primary winding terminals provide a means of monitoring the input voltage to the step up transformer, via circuitry known to the art, which the microprocessor can convert to a voltage at the electrodes using stored characteristics of the transformer. Parameters relating to the window type and dimensions for the above stated conversion from voltage applied to the electrodes to electric field in the gas can be entered into the microprocessor using input keys 80, digital I/O device 82 such as an RS 232 line, or other means. The microprocessor can convert the breakdown field to a percent gas content value using a relationship between gas mixture and breakdown field of the type shown in FIG. 1 stored in suitable compatible form. This value can then be displayed on a suitable display device 84, such as an LCD, stored internally or output through a digital I/O port.

It might also be convenient to rectify the AC voltage output at the secondary winding terminals of the step up transformer making use of known voltage multiplication circuitry in order to reduce the size of the transformer so that a DC voltage is delivered to the electrodes. Further, the accelerated positive ions of the discharge plasma can be directed by the polarity of the applied DC voltage to the glass surface which does not have a low emissivity, or other, coating.

It will be appreciated that various modifications and alterations may be made to the above described embodiments without departing from the spirit of the present invention. For example, while the description has focused on identifying breakdown by the measurement of the increase in electrode current, it will be understood by those skilled in the art that one could equally well use the breakdown voltage or the sound produced by the spark or the light given off or some other property associated with breakdown to key the recording of the voltage.

The embodiments of the invention in which an exclusive property of privilege is claimed are defined as follows:

1. An apparatus for determining the percentage gas content of an insulating glass window unit, comprising:
   means for generating a predetermined electrical voltage capable of causing a continuous electrical discharge in the gas contained within said window unit;
   plate electrode means electrically connected to said generating means for connection to the outer surfaces of opposed panes of said window unit;
   means for controlling said generating means;
   means for monitoring the voltage applied to said electrodes; and
   means for converting the monitored voltage into a percent gas content value.

2. An apparatus as defined in claim 1, said means for controlling said generating means including circuit means for producing an electrical signal for causing said generating means to increase its output voltage at a predetermined rate.

3. An apparatus as defined in claim 2, said means for controlling said generating means further including a voltage control circuit responsive to said electrical signal for producing said electrical voltage, said voltage control circuit having output terminals connected to said generating means and input terminals adapted to be connected to an AC source of power.

4. An apparatus as defined in claim 2, said means for controlling said generating means further including means for monitoring the input voltage of said generating means, detecting said electrical discharge and outputting a signal representative of the concentration of said gas within said window unit.

5. An apparatus as defined in claim 2, said means for controlling said generating means further including a microprocessor circuit.

6. An apparatus as defined in claim 2, said means for controlling said generating means further including an electrical control circuit.

7. An apparatus as defined in claim 1, said generating means including a step up transformer having a primary winding adapted to be connected to a source of electrical energy and a secondary winding adapted to be connected to said plate electrodes.

8. An apparatus as defined in claim 7, said means for controlling said generating means including circuit means for producing an electrical signal for causing said generating to increase its output voltage at a predetermined rate.

9. An apparatus as defined in claim 8, said means for controlling said generating means further including a voltage control circuit responsive to said electrical signal, said voltage control circuit having output terminals connected to said generating means and input terminals adapted to be connected to an AC source of power.

10. An apparatus as defined in claim 9, said means for controlling said generating means further including means for monitoring the input voltage of said generating means, detecting said breakdown voltage and outputting a signal representative of the concentration of said gas within said window unit.

11. An apparatus as defined in claim 10, said means for controlling said generating means further including a microprocessor circuit.

12. An apparatus as defined in claim 7, said means for controlling said generating means being a variac having output terminals connected to said primary winding.

13. An apparatus as defined in claim 1, said means for monitoring the voltage applied to said electrodes including a high voltage probe and volt meter connected across said electrodes.

14. An apparatus for determining the percentage gas content of an insulating glass window unit or the like, comprising:

a step-up transformer having a primary coil having a pair of input terminals adapted to be connected to a controlled source of electrical energy and a secondary coil having a pair of output terminals for producing a high voltage thereacross;

a pair of electrodes connected to said output terminals of said secondary coil for connection to opposed panes of said window unit;

means for monitoring the voltage applied to said input terminals;

means for determining the voltage applied to said electrodes;

means for detecting the breakdown voltage at which an electrical discharge occurs across said electrodes and converting said breakdown voltage to a value indicative of the percentage content of the gas contained within said unit.

15. A method of determining the percentage gas content of an insulating glass window unit or the like, comprising the steps of:

applying a voltage to opposed panes of said unit;

progressively increasing said voltage;

monitoring said voltage and recording the magnitude of the voltage at which a continuous electrical discharge is initiated between said panes; and converting said magnitude to a value indicative of the percentage gas content of the gas between said panes.

* * * * *